United States Patent [19]
Hack et al.

[11] Patent Number: 6,090,777
[45] Date of Patent: *Jul. 18, 2000

[54] METHOD TO REDUCE MYOCARDIAL INJURY DURING ACUTE MYOCARDIAL INFARCTION

[75] Inventors: Cornelis Erik Hack, Diemen; Willem Theodoor Hermens, Gronsveld, both of Netherlands

[73] Assignee: Stiching Centraal Laboratorium Van de Bloedtransfusiedienst Van Het Nederlandse Rode Kruis, Amsterdam, Netherlands

[*] Notice: This patent issued on a continued prosecution application filed under 37 CFR 1.53(d), and is subject to the twenty year patent term provisions of 35 U.S.C. 154(a)(2).

[21] Appl. No.: 08/604,933

[22] PCT Filed: Aug. 31, 1994

[86] PCT No.: PCT/NL94/00208

§ 371 Date: Apr. 2, 1996

§ 102(e) Date: Apr. 2, 1996

[87] PCT Pub. No.: WO95/06479

PCT Pub. Date: Mar. 9, 1995

[30] Foreign Application Priority Data

Sep. 1, 1993 [EP] European Pat. Off. .............. 93202572

[51] Int. Cl.⁷ .................................................. A61K 38/16
[52] U.S. Cl. .................. 514/2; 514/8; 530/380; 530/417
[58] Field of Search ............................ 514/2, 8; 530/380, 530/417

[56] References Cited

U.S. PATENT DOCUMENTS 4,915,945   4/1990   Pelzer et al. ............................ 530/380

FOREIGN PATENT DOCUMENTS

92/22320   12/1992   WIPO .

OTHER PUBLICATIONS

Reyes et al., Arch Inst Cardiol Mex 54(4): 327–332 (1984). Abstract.
Gardinali et al., Bollettino Dell Instituto Sieroterapico Milanese 61(1): 1–7 (Mar. 1982). Abstract, Feb. 1982.
Werns et al., Cardiovascular Drugs & Therapy 2(6): 761–769 (Jan. 1989). Abstract.
Langlois et al., Atherosclerosis 70: 95–105 (1988).
Guerrero et al., J. Clin. Invest. 91(6): 27542760 (Jun. 1993).
Engelberg, American Heart Journal 99(3): 359–372 (Mar. 1980).

*Primary Examiner*—Jean C. Witz
*Attorney, Agent, or Firm*—Hoffman & Baron, LLP

[57] ABSTRACT

A therapeutic or prophylactic treatment method of acute myocardial infarction, comprising administering exogenous C1-esterase inhibitor, alone or in combination with other drugs, to a patient with acute myocardial infarction or to a patient at risk for acute myocardial infarction. The treatment inhibits the inflammatory reaction, more specifically the activation of the complement system, which occurs in the course of acute myocardial infarction. The C1-esterase inhibitor may include C1-esterase inhibitor purified from plasma or other biological materials, or recombinant C1-esterase inhibitor, or recombinant variants derived therefrom, or recombinant constructs of other inhibitors having a specificity similar to C1-esterase inhibitor.

21 Claims, 8 Drawing Sheets

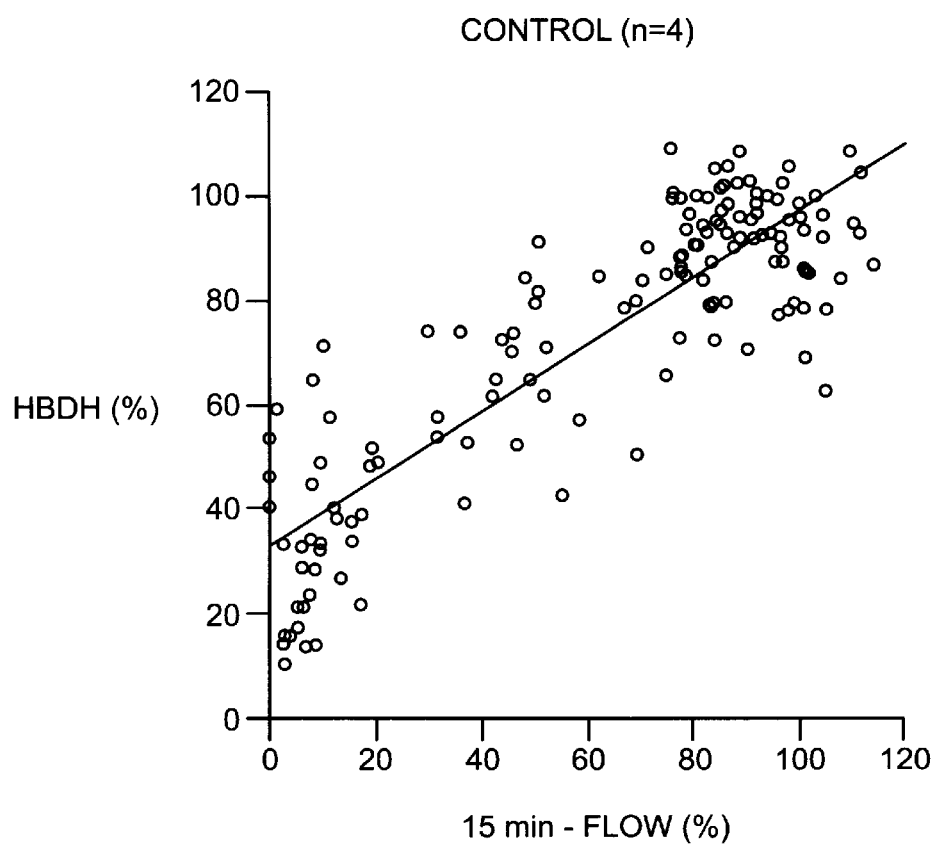
FIG. 1A ENDOCARDIAL SAMPLES

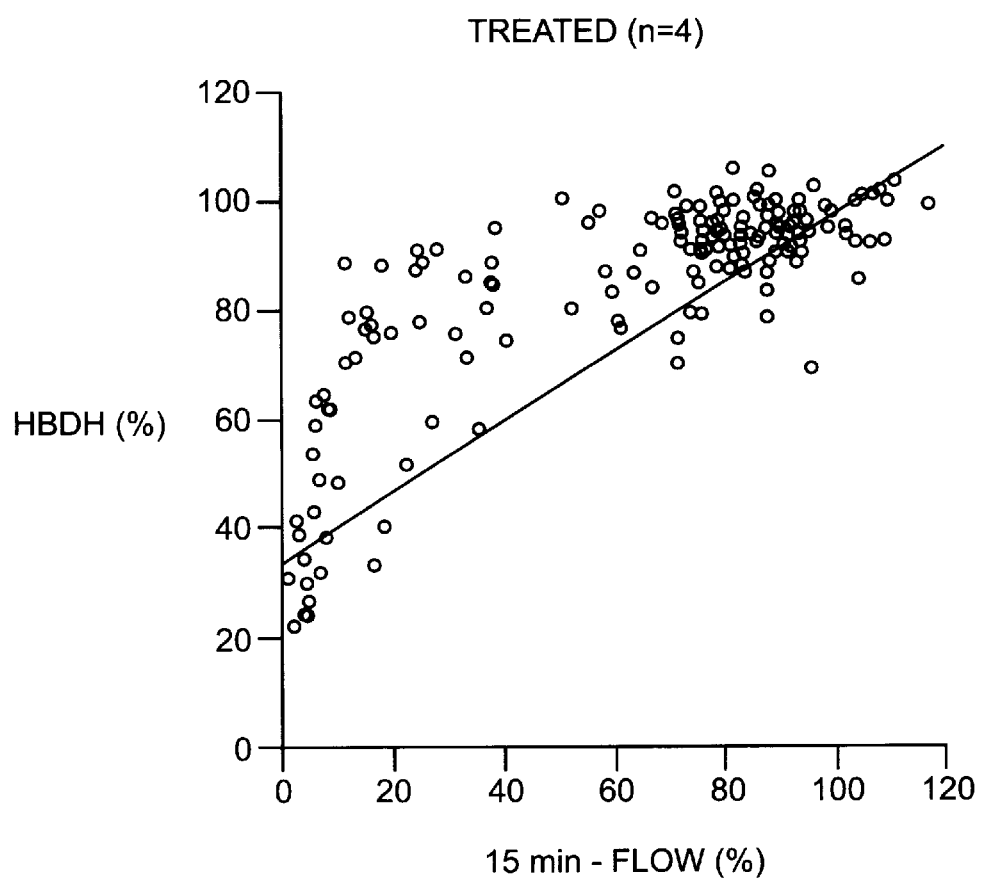
FIG. 1B  ENDOCARDIAL SAMPLES

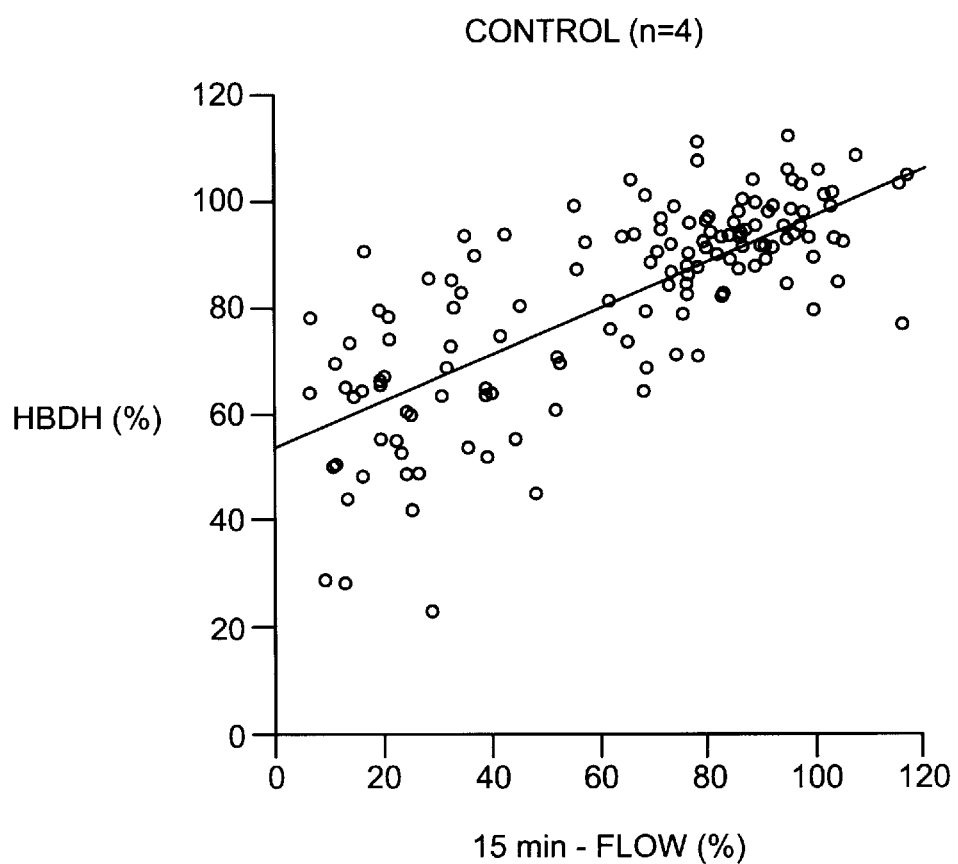
FIG. 2A  EPICARDIAL SAMPLES

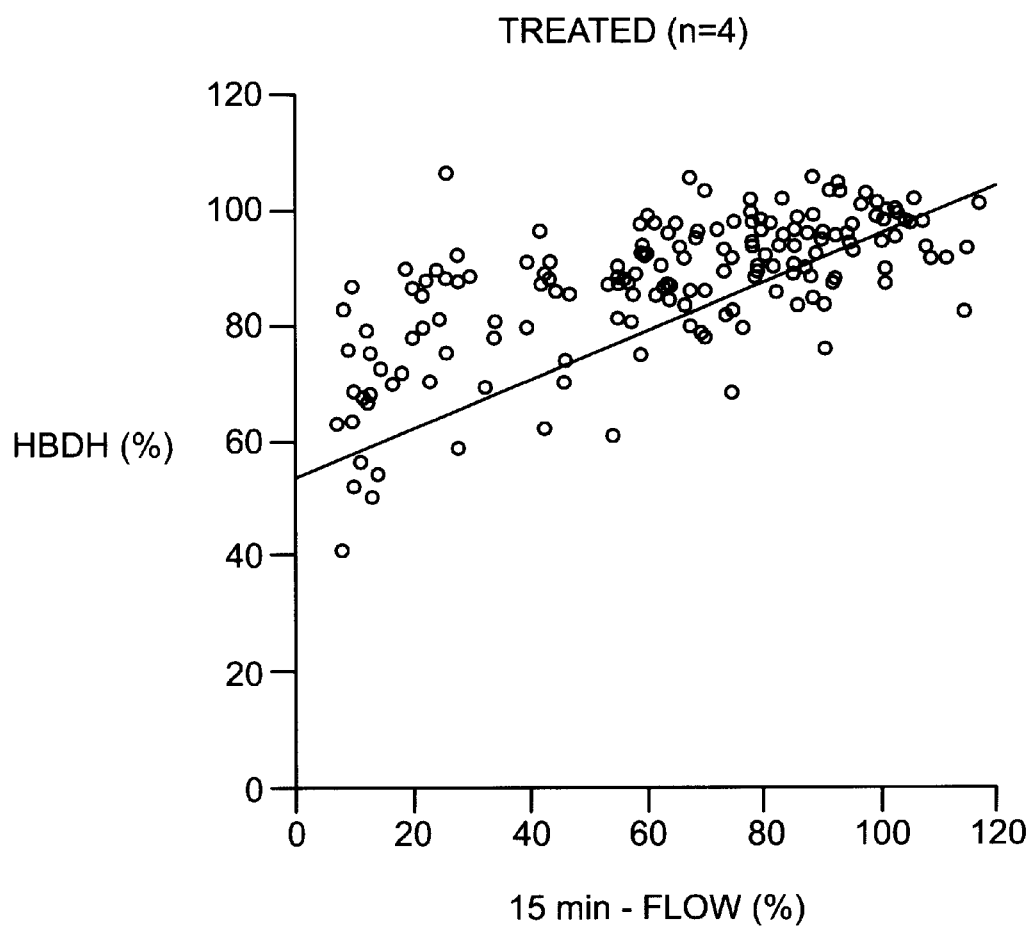

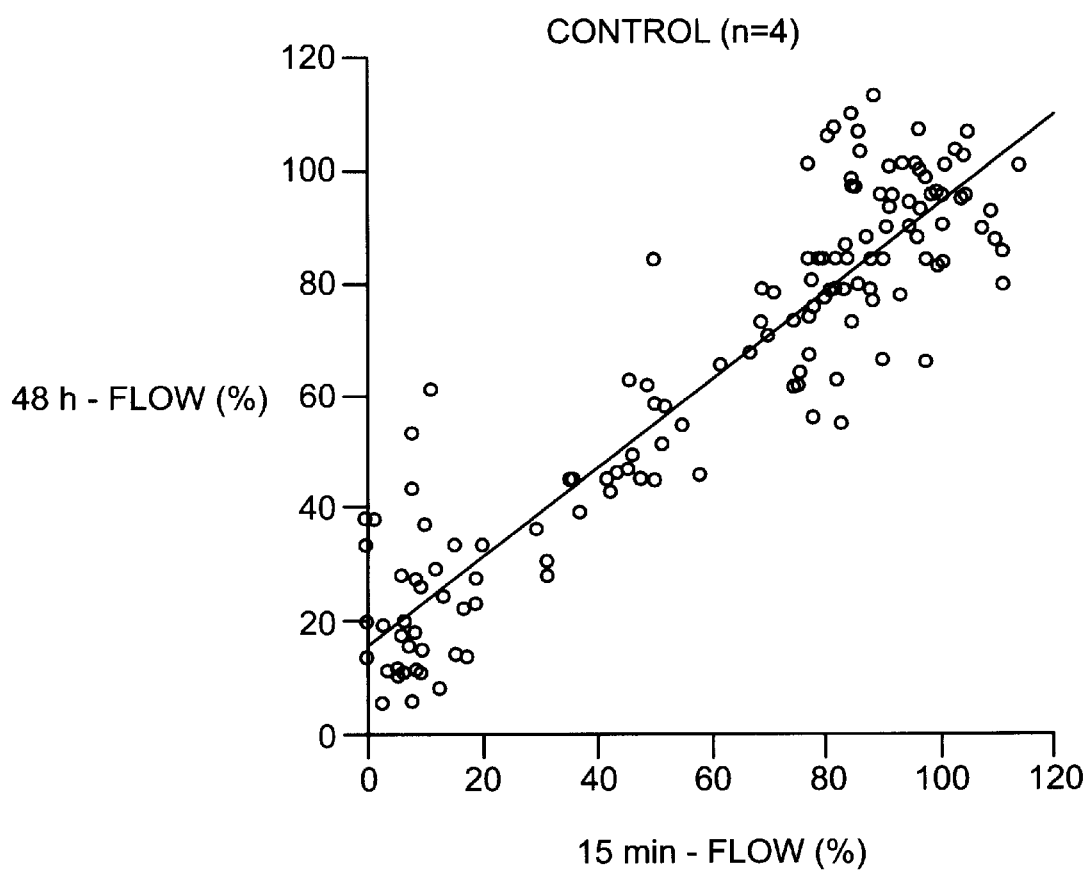
FIG. 3A ENDOCARDIAL SAMPLES

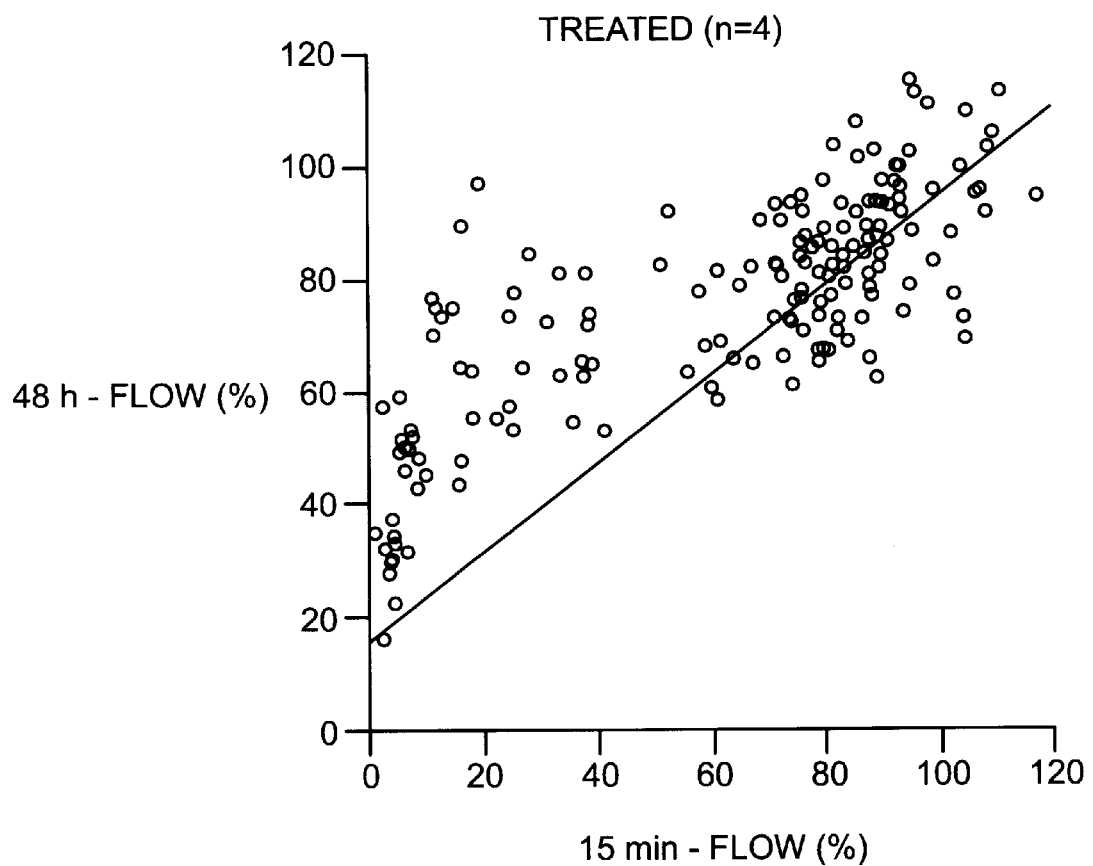
FIG. 3B ENDOCARDIAL SAMPLES

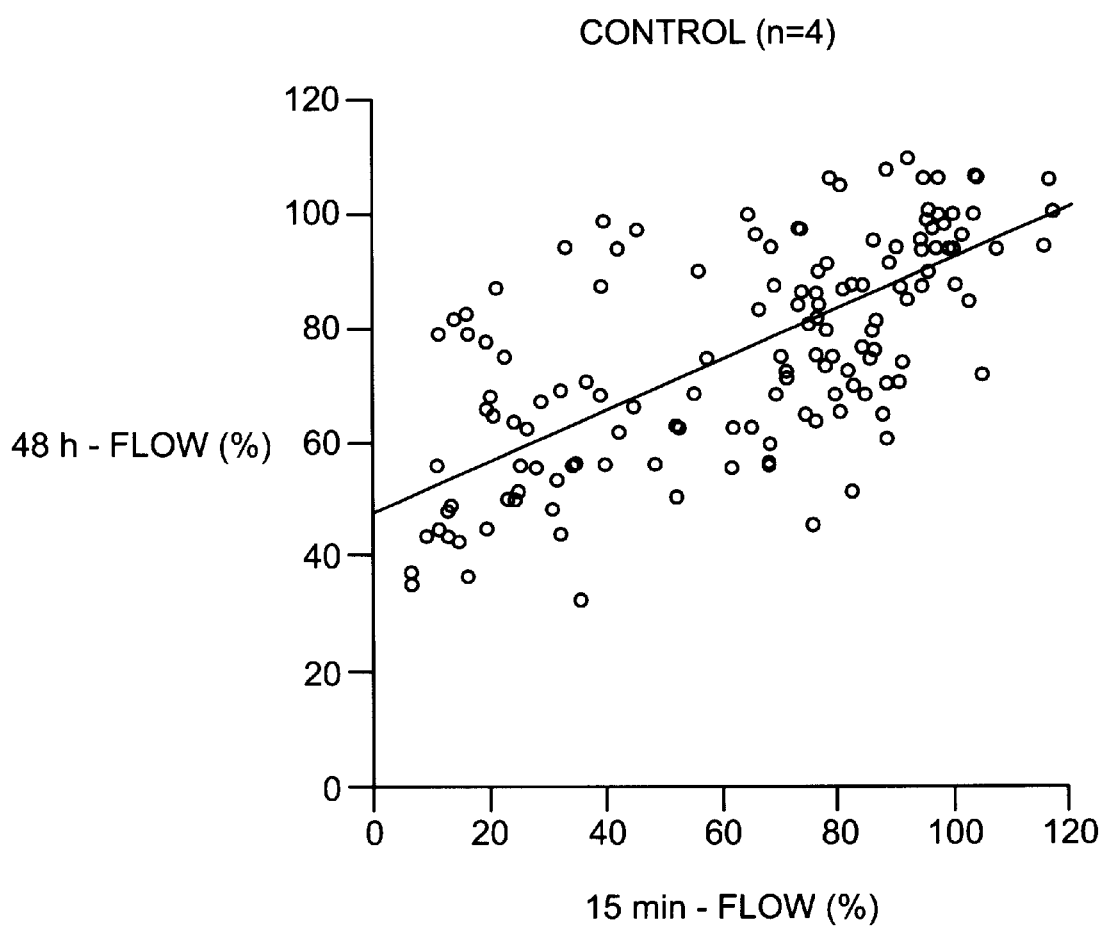
FIG. 4A  EPICARDIAL SAMPLES

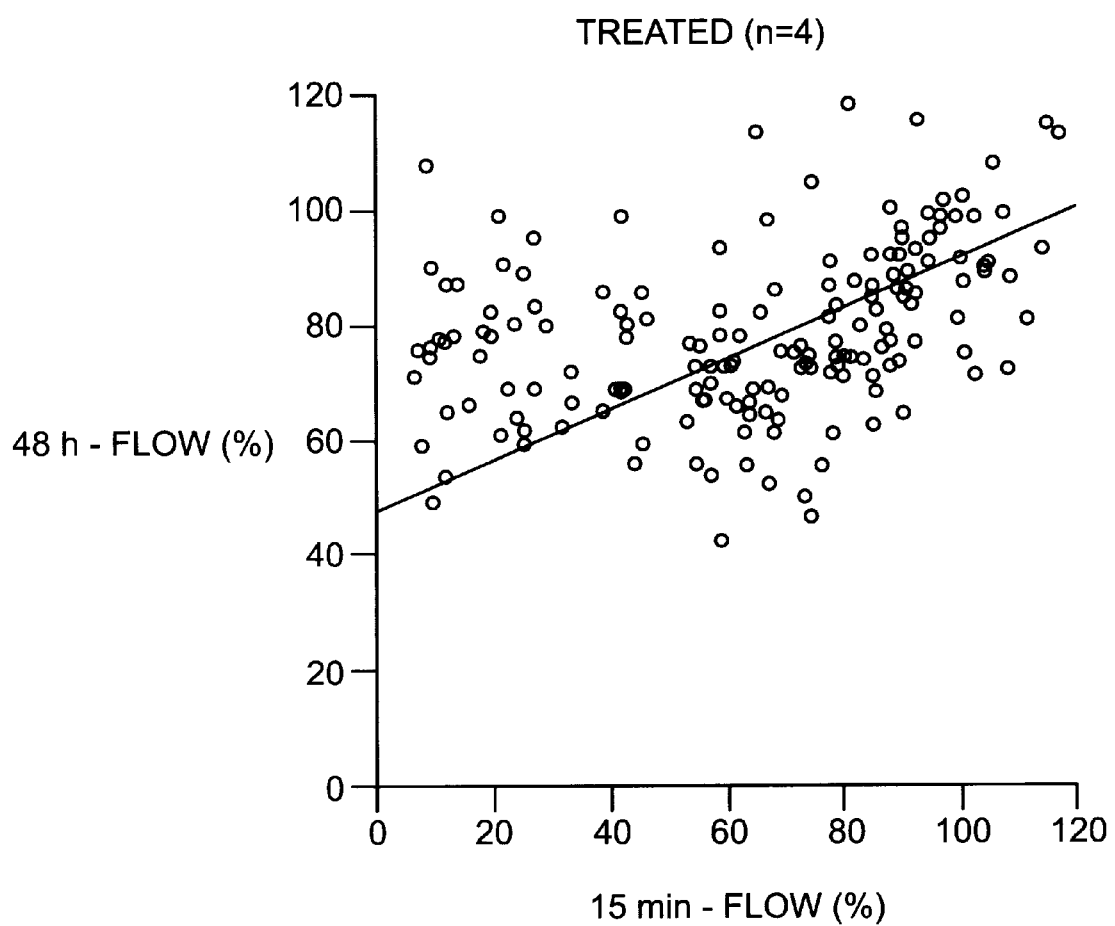
FIG. 4B  EPICARDIAL SAMPLES

METHOD TO REDUCE MYOCARDIAL INJURY DURING ACUTE MYOCARDIAL INFARCTION

FIELD OF THE INVENTION

This invention is in the field of immunology/cardiology/biochemistry, and describes more particularly a method to reduce myocardial cell injury during acute myocardial infarction.

BACKGROUND OF THE INVENTION

Mechanical failure of heart muscle is one of the leading causes of in-hospital deaths in patients with acute myocardial infarction (AMI). Friedberg C. K., 1968, *Circulation* 39 suppl. IV: 252. An important determinant in the development of such failure is the amount of necrotic tissue in the jeopardized myocardium. Pare D. L. et al., 1971, *New Eng J Med* 285: 133. Experimental studies in animals have shown that irreversible myocardial cell injury starts about 30 minutes after occlusion of coronary vessels and proceeds for hours. Maroko P. R. et al., 1973, *Ann Int Med* 79: 720. However, even interventions given as late as 6 hours after cornary occlusion are able to reduce infarction size after AMI by about 35% compared to untreated control animals. Libby P. et al., 1973, *J Clin Invest* 52: 599. Electrocardiographic studies indicate that also in humans a substantial amount of myocardial tissue may not become irreversibly injured until hours or even days after occlusion of the coronary vessel, i.e. at a time that most patients will have been admitted to a hospital. Reid P. R. et al., 1974, *New Engl J Med* 290: 123. A number of experimental and clinical studies have attempted to minimize infarction size by reducing the myocardial necrosis that occurs in the later stages of AMI. Maroko P. R. et al., 1973, *Ann Int Med* 79: 720.

The later phase of myocardial cell injury likely results from an ensuing acute inflammatory reaction characterized by infiltration of neutrophilic granulocytes (neutrophils). Entman M. L. et al., 1991, *FASEB J* 5: 2529. Initially, the importance of an inflammatory reaction in mediating myocardial cell injury during AMI was recognized in animal studies which showed that corticosteroids could reduce infarction size by 20 to 35%. Libby P. et al., 1973, *J Clin Invest* 52: 599;Maclean D. et al., 1978,*J Clin Invest* 61: 541. However, clinical application of methyl-prednisolone in AMI to minimize myocardial necrosis, was not successful mainly because this treatment interfered with scar formation and healing, leading in some patients to the development of aneurysm and rupture of the ventricle wall. Roberts R. et al., 1976, *Circulation* 53 *Suppl. I:* 204. A similar effect has been observed in long-term experiments in rats. Maclean D. et al., 1978, *J Clin Invest* 61: 541. These disappointing results tuned down further clinical studies that aimed at reducing infarction size by attenuating the inflammatory reaction following AMI.

The inflammatory reaction which occurs in the course of AMI comprises some important events: the local production of chemotactic factors, the infiltration and activation of neutrophils, the local production of cytokines (such as tumor necrosis factor-$\alpha$ and interleukin-6) to enhance adherence of neutrophils to cardiac myocytes, and the local activation of the complement system. Entman M. L. et al., 1991, *FASEB J* 5: 2529.

A role of complement activation in AMI was initially suggested by Hill and Ward who provided evidence that complement activation products generated in the infarcted myocardium were responsible for the infiltration of neutrophils. Hill J. H. et al., 1970, *J Exp Med* 131: 885. Later studies showed that plasma levels of activated complement components are increased in patients with AMI and that several complement components become localized in the infarcted area during the course of AMI, as has been demonstrated both in animals as well as in patients. Pinckard R. N. et al., 1975, *J Clin Invest* 56: 740; Langlois P. F. et al., 1988, *Atherosclerosis* 70: 95; Yasuda M. et al., 1990, *Circulation* 81: 156; Pinckard R. N. et al., 1980, *J Clin Invest* 66: 1050; McManus L. M. et al., 1983, *Lab Invest* 48: 436; Schafer H. et al., 1986,*J Immunol* 137: 1945; Hugo F. et al., 1990, *Clin Exp Immunol* 81: 132.

Furthermore, a number of studies have demonstrated that complement activation products such as the anaphylatoxins and TCC may have deleterious effects on the myocardium by mechanisms dependent and independent of neutrophils, such as the local production of thromboxane A2 and peptidoleukotrienes LTC4 and LTD4, the release of histamine, plasmalemmal disruption and the activation of neutrophils in the coronary circulation with subsequent plugging of capillary vessels, formation of toxic oxygen radicals and the release of proteolytic enzymes. These mechanisms may lead to vasoconstriction, impaired micro-circulation, an increase in coronary perfusion pressure, and result in ischaemia, contractile failure of the myocardium, tachycardia and impairment of atrioventricular conduction. Del Balzo U. et al., 1984, *Proc Natl Acad Sci USA* 82: 886; Martin S. E. et al., 1988, *Circ Res* 63: 483; Ito B. R. et al., 1989, *Circ Res* 65: 1220; Del Bazzo U. et al., 1989, *Circ Res* 65: 847; Ito B. R. et al., 1990, *Circ Res* 66: 596; Stahl G. L. et al., 1990, *Circ Res* 66: 1103; Engler R. L. et al., 1991, *FASEB J* 5: 2983; Homeister J. W. et al., 1992, *Circ Res* 71: 303.

The molecular mechanism of the observed activation of complement during AMI is not clear, although released mitochondrial constituents, presumably membranes, have been frequently claimed to induce the activation. Pinckard R. N. et al., 1973, *J Immunol* 110: 1376; Pinckard R. N. et al., 1975, *J Clin Invest* 56: 740; Giclas P. C. et al., 1979, *J Immunol* 122: 146; Storrs S. B. et al., 1981, *J Biol Chem* 256: 10924; Rossen R. D. et al., 1988, *Circ Res* 62: 572; Kagiyama A. et al., 1989, *Circ Res* 64: 607. However, it should be noted that most of these studies dealt with activation of complement following reperfusion of ischaemic myocardium rather then that following ischaemia due to permanent occlusion of coronary vessels. The deleterious effects of complement activation products on the myocardium have been substantiated by observations that in animal models complement depletion prior to or shortly after permanent occlusion of a coronary vessel significantly reduces the amount of myocardial necrosis. Maroko P. R. et al., 1978, *J Clin Invest* 61: 661; Maclean D. et al., 1978, *J Clin Invest* 61: 541; Pinckard R. N. et al., 1980,*J Clin Invest* 66: 1050; Crawford H. R. et al., 1988, *Circulation* 78: 1449. None of the studies investigating the effect of complement inhibition on myocardial damage after permanent occlusion of a coronary vessel have used a true inhibitor of the complement cascade, all these studies were done with an agent, i.e. Cobra Venom Factor, that intravascularly activates and depletes the system. However, this method of complement inhibition/depletion cannot be used in clinical situations considering the inherent dangers of intravascular complement activation such as the development of adult respiratory distress. Goldstein IM, 1992, In: Gallin JI, Goldstein IM, Snyderman R (eds): *Inflammation: Basic Principles and Clinical Correlates,* New York, Raven Press, p.63; Craddock P. R. et al., 1977, *New Eng J Med* 296: 769; Stimler N. P. et al., 1980, *Am J Pathol* 100: 327; Hosea S.

F. et al., 1980, *J Clin Invest* 66: 375; Ward P. A. et al., 1985, *J Clin Invest* 76: 517.

The discussion above deals with activation of the complement system during permanent occlusion of coronary vessels. However, it is now generally accepted to treat patients with AMI with thrombolytic therapy or coronary angioplasty to reperfuse the jeopardized myocardium. The sooner after the occlusion this therapy is given, the more effective it is to salvage the ischaemic myocardium. Clinical studies indicate that more than half of the effect of thrombolytic therapy is lost when treatment is delayed 60–75 minutes. Hermens WTh et al., 1992, *Lancet* 3: 1297. However, more than 90% of the patients with AMI do not reach the hospital within 75 minutes after the occlusion of a coronary artery and, therefore, will hardly benefit from thrombolytic therapy.

There is ample evidence that reperfusion of ischaemic myocardium itself may induce an inflammatory reaction, also known as ischaemic-reperfusion injury, which is caused by activation of complement and neutrophils and the generation of oxygen radicals. Rossen R. D. et al., 1985, *Circ Res* 57: 119; Rossen R. D. et al., 1988, *Circ Res* 62: 572; Dreyer W. J., 1989, *Circ Res* 65: 1751; Dreyer W. J. et al., 1992, *Circ Res* 71: 1518; Lucchesi BR et al., 1989, *J Mol Cell Cardiol* 21: 1271; Engler R et al., 1989, *Circulation* 79: 1137. This ischaemic-reperfusion injury may damage the cardiac tissue and limit the beneficial effects of a restored circulation. Herdson PB et al., 1965, *Am J Pathol* 46: 367. Reperfusion therapy in AMI can, therefore, be regarded as a "double edged sword" and is better not applied as late as 2 hours or more after the onset of AMI.

Until now there are no clinical studies in patients with AMI showing activation of complement due to reperfusion of the infarcted myocardium. However, inhibition of complement in these patients may be beneficial since in rats undergoing reperfusion of ischaemic myocardium, treatment with a recombinant soluble form of the human complement receptor type 1 has been shown to reduce myocardial infarction size considerably. Weisman H. F. et al., 1990, *Science* 249: 146.

To date there is no report in literature describing a beneficial effect of a complement inhibitor (i.e., a protein or substance which inhibits a [activated] complement protein rather then depletes it by activation) on the myocardial infarction size after permanent occlusion of a coronary vessel. The present invention describes a simple method to reduce myocardial infarction size by administering a naturally occurring inhibitor of the activated first component of complement.

SUMMARY OF THE INVENTION

It has now been found that administration of the serine-proteinase inhibitor C1-esterase inhibitor reduces the size of myocardial infarction when given as late as 2 hours following occlusion of a coronary vessel.

Therefore, the present invention contemplates a therapeutic or prophylactic treatment method of AMI, which method comprises administering exogenous C1-esterase inhibitor, alone or in combination with other drugs, to a patient with acute myocardial infarction or to a patient at risk for acute myocardial infarction.

The treatment is applicable, independent from whether or not the patient is receiving medical or surgical treatment to restore blood flow to the jeopardized myocardium. In particular, the invention is also applicable in patients who, because of the time elapsed between the onset of AMI and the admission to a hospital, may not (or not anymore) be treated by reperfusion therapy. Thus, the invention provides an alternative method to treat these patients (more than 90% of all patients with AMI!), since it is still effective in reducing myocardial tissue injury when given as late as 2 hours after the occlusion of a coronary vessel.

Exemplary C1-esterase inhibitor may be derived from human plasma or any other biological source, or recombinant C1-esterase inhibitor, or mutants derived therefrom, or recombinant proteinase inhibitor with specificity for the activated form of the first component of complement.

Examples of other drugs which may be administered in combination with C1-esterase inhibitor are substances which improve the blood flow to the myocardium, such as tissue plasminogen activator, urokinase and streptokinase, and substances having anti-inflammatory properties, such as oxygen radical scavengers and cytokine antagonists.

The invention will be more fully understood after a consideration of the following description of the invention.

BRIEF DESCRIPTION OF THE DRAWINGS

The effect of administering plasma-derived human C1-esterase inhibitor on myocardial damage of AMI was studied in dogs that underwent a permanent ligation of the left anterior descending coronary artery (LAD). Forty-eight hours after occlusion the animals were killed and the hearts excised. The ischaemic myocardium was cut into pieces of about 1 gram. Myocardial damage was assessed by measuring the residual α-hydroxybutyrate dehydrogenase (HBDH) activity in each piece of myocardial tissue. The blood flow in each piece of myocardium at 15 minutes and at 48 hours was measured by injecting labeled microspheres intravenously 15 min and 48 hours after occlusion and counting radio-activity of the pieces. The results were expressed as %, 100% being the value observed for normal myocardium. The results shown were obtained from 4 dogs that received C1-esterase inhibitor at 2 and 8 hours after occlusion (treated) and 4 dogs that did not receive C1-esterase inhibitor (control).

FIGS. 1A and 1B show that for the same degree of initial ischaemia (flow at 15 minutes) the hearts of the animals treated with C1-esterase inhibitor had lost about 50% less muscle enzyme than the controls.

FIGS. 2A and 2B show the same as FIGS. 1A and 1B except that the results shown were obtained with epicardial tissue specimens.

FIGS. 3A and 3B show that the reduction of myocardial enzyme depletion in animals treated with C1-esterase inhibitor runs parallel to about 50% recovery of blood flow in the infarcted area during the first 48 hours, in spite of continued LAD ligation.

FIGS. 4A and 4B show the same as FIGS. 3A and 3B except that the results shown were obtained with epicardial tissue specimens.

DETAILED DESCRIPTION OF THE INVENTION

The invention provides a method to inhibit the inflammatory reaction, more specifically the activation of the complement system, which occurs in the course of acute myocardial infarction. The preferred inhibitor is C1-esterase inhibitor, which may include C1-esterase inhibitor purified from plasma, or recombinant C1-esterase inhibitor, or recombinant variants derived therefrom, or recombinant constructs of other inhibitors having a specificity similar to C1-esterase inhibitor.

Several patent documents and scientific articles are referred to below that discuss various aspects of the materials and methods used to realize the invention. It is intended that all of the references be entirely incorporated by reference.

Basic for the present invention is the realization that activation of complement causes substantial myocardial damage during AMI, independently from whether or not medical treatment, such as thrombolytic therapy, is instituted to re-open the occluded coronary vessels, and that inhibition of this activation would reduce or prevent this myocardial damage. The preferred method to inhibit complement activation in persons suffering from AMI would be administering plasma-derived C1-esterase inhibitor, but by no means should this invention be constructed so narrowly. Virtually every method to inhibit complement activation by inhibiting the activity of the first component of complement is intended to come into the scope of this invention.

To more clearly define the present invention, it will be described in three sections. The first section contains definitions of particular terms as they will be employed herein. These definitions are generally consistent with their usage in the art. The second section describes more specifically the various C1-esterase inhibitor molecules which are intended to come into the scope of the invention. The third section describes the method to administer exogenous C1-esterase inhibitor to a patient with AMI.

Definitions

As used herein, the phrase "complement system" refers to a set of proteins, most of which circulate in blood as inactive precursor proteins, also known as factors. During activation of the system, one factor activates the subsequent one by limited proteolysis and so on. This activation process resembles a cascade and, therefore, the complement system is also considered as one of the major plasma cascade systems, the other being the coagulation, the fibrinolytic and the contact systems. The physiological role of the complement system is to defend the body against invading microorganisms. The system may become activated via two pathways, a classical and an alternative pathway, which both can activate a common terminal pathway. Cooper N. R., 1985, *Adv Immunol* 37: 151; Muller-Eberhard H. J. et al., 1980, *Adv Immunol* 29: 1; Muller-Eberhard H. J., 1992, In: Gallin JI, Goldstein IM, Snyderman R (eds): *Inflammation: Basic Principles and Clinical Correlates,* New York, Raven Press, p.33. A number of biologically active peptides, also known as the anaphylatoxins, are generated during activation of complement. Vogt W., 1986, *Complement* 3: 177. The anaphylatoxins, in particular C3a and C5a, are chemotactic for neutrophils and able to aggregate, activate and degranulate these cells. Vogt W., 1986, *Complement* 3: 177; Goldstein IM, 1992, In: Gallin JI, Goldstein IM, Snyderman R (eds): *Inflammation: Basic Principles and Clinical Correlates,* New York, Raven Press, p.63.Furthermore they may enhance vasopermeability, stimulate adhesion of neutrophils to endothelium, activate platelets and induce the production of vasoactive eicosanoids, thromboxane A2 and peptidoleukotrienes such as LTC4, LTD4 and LTE4. Also the so-called terminal complement complexes (TCC), formed upon activation of the common pathway, have important effects such as the capacity to kill cells. Muller-Eberhard H. J., 1986, *Ann Rev Immunol* 4: 503. Activation of the classical pathway of complement starts with activation of the first component, which consists of a macromolecular complex of 5 proteins, one C1q, two C1r and two C1s proteins. The C1q protein of the C1 complex binds to an activator, for example immune complexes, which leads to activation of both C1r and both C1s subcomponents. Cooper N. R., 1985, *Adv Immunol* 37: 151. During activation the C1r and C1s proteins are converted from a single peptide-chain inactive protein to a two-chain active serine proteinase. Cooper N. R., 1985, *Adv Immunol* 37: 151. The activated C1complex then activates the complement factors C4 and C2, which both form a complex that can activate C3, the complement factor. Several plasma proteins can inhibit activation of the classical pathway of complement, notably, C1-esterase inhibitor, C4-binding protein and the serine-proteinase factor I. Muller-Eberhard H. J., 1992, In: Gallin JI, Goldstein IM, Snyderman R (eds): *Inflammation: Basic Principles and Clinical Correlates,* New York, Raven Press, p.33; Cooper N. R., 1985, *Adv Immunol* 37: 151.

As used herein, the phrase "contact system" refers to a set of proteins, which circulate in blood as inactive precursor proteins, and which is also known as the contact system of coagulation or the kallikrein-kinin system. Colman R. W., 1984,*J Clin Invest* 73: 1249; Kaplan A. P. et al., 1987, *Blood* 70: 1; Kozin F., et al, 1992, In: Gallin JI, Goldstein IM, Snyderman R (eds): *Inflammation: Basic Principles and Clinical Correlates,* New York, Raven Press, p.103. The contact system also belongs to the major plasma cascade systems, and is often regarded as one of the two pathways via which the coagulation system can be activated, the so-called extrinsic pathway of coagulation being the other. The physiological role of the contact system is not precisely known, although it is known that this system may become activated in inflammatory conditions. Colman R. W., 1984, *J Clin Invest* 73: 1249; Kaplan A. P. et al., 1987, *Blood* 70: 1; Kozin F., et al, 1992, In: Gallin JI, Goldstein IM, Snyderman R (eds): *Inflammation: Basic Principles and Clinical Correlates,* New York, Raven Press, p.103.. Activation of the contact system starts with binding of factor XII, also known as Hageman factor, to an activator. Subsequently, bound factor XII may become activated, during which process it is converted from a single-chain inactive to a two-chain active serine proteinase. Tans G. et al., 1987, *Sem Thromb Hemost* 13: 1. Activated factor XII then activates prekallikrein, that together with its cofactor high molecular weight kininogen is bound to the activator, into the active serine proteinase kallikrein. Kallikrein in turn may activate bound but not yet activated factor XII (reciprocal activation), and/or factor XI, which in turn can activate factor IX to start activation of coagulation. Cochrane C. G. et al., 1982, *Adv Immunol* 3: 290; Colman R. W., 1984,*J Clin Invest* 73: 1249; Kaplan A. P. et al., 1987, *Blood* 70: 1; Kozin F., et al, 1992, In: Gallin JI, Goldstein IM, Snyderman R (eds): *Inflammation: Basic Principles and Clinical Correlates,* New York, Raven Press, p.103. Activation of the contact system is controlled by the same protein which also inhibits the classical complement pathway, C1-esterase inhibitor. During activation of the contact system several biologically active components are formed such as bradykinin, kallikrein and activated factor XII, which may enhance activation and degranulation of neutrophils, increase vasopermeability and decrease vascular tonus. Colman R. W., 1984, *J Clin Invest* 73: 1249; Kozin F., et al, 1992, In: Gallin JI, Goldstein IM, Snyderman R (eds): *Inflammation Basic Principles and Clinical Correlates,* New York, Raven Press, p.103.

As used herein, the phrase "C1-esterase inhibitor" refers to a protein that is present in blood and is the main inhibitor of the classical pathway of complement and of the contact system. C1-esterase inhibitor can inhibit the activated form of the first component of complement and activated factor XII, and it is also a major inhibitor of kallikrein. Schapira M.

et al., 1985, Complement 2: 111; Davis A. E., 1988, *Ann Rev Immunol* 6: 595; Sim R. B. et al., 1979, *FEBS Lett* 97: 111; De Agostini A. et al., 1984, *J Clin Invest* 73: 1542; Pixley R. A. et al., 1985, *J Biol Chem* 26: 1723; Schapira M. et al., 1982, *J Clin Invest* 69: 462; Van der Graaf F. et al., 1983, *J Clin Invest* 71: 149; Harpel P. C. et al., 1975, *J Clin Invest* 55: 593. In addition, C1-esterase inhibitor may inhibit activated factor XI, tissue-type plasminogen activator and plasmin. Meijers J. C. M. et al., 1988, *Biochemistry* 27: 959; Harpel P. C. et al., 1975, *J Clin Invest* 55: 149; Booth N. A. et al., 1987, *Blood* 69: 1600.

C1-esterase inhibitor inhibits proteinases by forming stable complexes with these proteinases, which are rapidly cleared from the circulation. De Smet B. J. G. L. et al., 1993, *Blood* 81: 56. Full-length genomic and cDNA coding for C1-esterase inhibitor has been cloned. Bock S. C. et al., 1986, *Biochemistry* 25: 4292; Carter P. E. et al., 1988, *Eur J Biochem* 17: 163. Functional recombinant C1-esterase inhibitor protein has been expressed in COS cells and found to be similar to the plasma protein. Eldering E. et al., 1988, *J Biol Chem* 263: 11776. In addition, several variants of recombinant C1-esterase inhibitor with amino acid mutations at the P1 and the P3 and/or P5 position of the reactive centre have been expressed in the same system. Eldering E. et al., 1988, *J Biol Chem* 263: 11776; Eldering E. et al., 1993, *J Biol Chem* 267: 7013; Eldering E. et al., 1993, *J Clin Invest* 91: 1035; Patent Cetus Corp, U.S. Pat. No. 6,17,920. Moreover, some variants isolated from patients with hereditary angioedema have been cloned and expressed in the same system. Davis A. E. et al., *Nature Genetics* 1: 354.

C1-esterase inhibitor belongs to a superfamily of homologous proteins which together are known as the serineproteinase inhibitors, also called serpins. Travis J. et al., 1983, *Ann Rev Biochem* 52: 655; Carrel R. W. et al., 1985, *Trends Bioch Sci* 10: 20. The serpins share a similar mechanism of inhibition, which is characterized by forming stable bi-molecular complexes with the proteinase to be inhibited. In these complexes the active site of the proteinase is bound to the so-called reactive centre of the serpin and hence rendered inactive. Travis J. et al., 1983, *Ann Rev Biochem* 52: 655. Serpins have specificity for certain proteinases and this specificity is in part due to the amino acid sequence of the reactive centre. A number of studies have shown that it is possible to alter the specificity of a serpin by changing the amino acid sequence of the reactive centre and/or other parts of the inhibitor, for example by site-directed mutagenesis. Owen M. C. et al., 1983, *New Eng J Med* 30: 694; Carrel R. W. et al., 1985, *Trends Bioch Sci* 10: 20; Courtney M. et al., 1985, *Nature* 313: 77; George P. M. et al., 1989, *Blood* 73: 490; Rubin H. et al., 1990, *J Biol Chem* 265: 1199; Holmes W. E. et al., 1987, *Biochemistry* 26: 5133. Although a recombinant variant of serpins other than C1-esterase inhibitor with a specificity for activated C1 has not been described, it is reasonable to expect that such inhibitors can be constructed.

As used herein the phrase "acute myocardial infarction" ("AMI") refers to a common clinical condition caused by necrosis of myocardial tissue. This condition is well-known in the art and is characterized by the occurrence of pain, in most cases precordial, characteristic electrocardiographic changes and an increase in plasma levels of intracellular enzymes released by the necrotic cardiac tissue such as creatinine phosphokinase and α-hydroxybutyrate dehydrogenase. AMI may be accompanied by hypotension, circulatory failure, pulmonary edema and arhythmias. In most cases, but not exclusively, AMI results from vascular injury and thrombosis in the coronary vessels, which causes these vessels to become occluded with subsequent impaired blood flow to the jeopardized myocardium. Fuster V. et al., 1992, *New Enal J Med* 326: 242 and 310. In most cases the time of the occlusion of the coronary vessel can be estimated from the medical history, the course of plasma levels of intracellular heart muscle enzymes and electrocardiographic changes.

II. C1-esterase Inhibitor Preparations

The activity of C1-esterase inhibitor in plasma or in purified preparations can be measured with several assays including chromogenic and esterolytic assays, in which the inhibition of conversion of substrates by active C1s is monitored. These assays are well-known in the art. Also, a radioimmunoassay, in which the binding of C1-esterase inhibitor to solid-phase bound active C1s is assessed, can be used to measure levels of functional C1-esterase inhibitor. Nuijens J. H. et al., 1989, *J Clin Invest* 84: 443. Levels of functional C1-esterase inhibitor can be expressed in various ways. Here Units per milliliter (U/ml) will be used where one U/ml is the concentration of functional C1-esterase inhibitor present in pooled normal plasma, which is approximately 270 µg per ml of plasma. Nuijens J. H. et al., 1989, *J Clin Invest* 84: 443.

Intended to come into the scope of the invention is the application of the following forms of C1-esterase inhibitor molecules: native C1-esterase inhibitor purified from human or animal plasma or any other biological source, or fragments derived therefrom that maintain biological activity; recombinant native C1-esterase inhibitor, human or animal, or variants or fragments therefrom that maintain biological activity; or recombinant inhibitors manipulated to inhibit the activated form of the first component of complement.

The C1-esterase inhibitor preparation is dissolved into a pharmaceutically acceptable vehicle, and in the preferred embodiment of this invention, given by intravenous injection. Such vehicles are well-known in the art and examples include water, saline, dextrose solution, Ringer's solution and solutions containing small amounts of human serum albumin. It will, of course, be understood that intended to come within the scope of this invention is virtually any method of administering C1-esterase inhibitor to yield sufficient concentrations of this inhibitor in the jeopardized myocardium.

III. Treatment of Acute Myocardial Infarction with C1-esterase Inhibitor

The C1-esterase inhibitor preparation described herein, alone or in combination, may be used to treat a host organism either suffering from AMI, or at risk for developing this condition.

In the preferred embodiment of the invention C1-esterase inhibitor is administered intravenously to a patient with AMI to yield sufficient amounts of C1-esterase inhibitor in the jeopardized myocardium during the first 24 hours after occlusion of the coronary vessel. In most cases this can be achieved by administering C1-esterase inhibitor until plasma levels of functional C1-esterase inhibitor are within the range of 2 to 2.5 U per ml. For most patients, two intravenous injections of 30 to 40 U of C1-esterase inhibitor per kg of body weight each, for example at the time the patient is admitted to the hospital and 6 hours later, will yield this plasma level. In case of clinical and biochemical evidence for further ongoing necrosis of myocardial tissue, as manifested by the course of intracellular heart muscle enzymes or electrocardiographic changes, additional gifts of C1-esterase inhibitor can be given. C1-esterase inhibitor therapy can be given to patients who, because of the time elapsed between the onset of AMI and admission to the hospital, may not benefit anymore from reperfusion therapy.

Activation of the complement system not only contributes to the myocardial tissue damage due to permanent occlusion of a coronary vessel, but also to that caused by reperfusion of the ischaemic tissues following coronary angioplasty or treatment with thrombolytic agents. Therefore, patients with AMI may be treated with C1-esterase inhibitor independent from whether they do or do not receive medical or surgical treatment to re-open coronary vessels. Typically, a patient is admitted to a hospital because of AMI. When appropriate, the patient may receive thrombolytic therapy or acute percutaneous transluminal coronary angioplasty, which procedures are well-known in the art, and at the same time C1-esterase inhibitor may be injected intravenously at a dose of 30 to 40 U per kg of body weight. This may be followed by a second gift of C1-esterase inhibitor at a similar concentration 6 hours thereafter. In another embodiment of the invention C1-esterase inhibitor administration treatment is instituted in a patient with AMI, who does not receive angioplasty or thrombolytic therapy. Typically, such a patient may receive an intravenous injection of C1-esterase inhibitor at a dose of 30 to 40 U per kg of body weight upon admission to the hospital, which administration may be repeated 6 hours thereafter.

Patients with partial occlusions of the coronary vessels may receive medical therapy such as percutaneous transluminal coronary angioplasty, which are accompanied by temporary complete occlusion of the coronary vessels. Reperfusion of the jeopardized myocardium may be accompanied by inflammatory reactions which may affect the function of the myocardial vessels. Intended to be within the scope of this invention is the prophylactic treatment of these patients by administering them a single intravenous injection of C1-esterase inhibitor at a dose of 30 to 40 U per kg of body weight.

Having described what the applicants believe their invention to be, the following examples will be presented to illustrate the invention. The examples are intended as illustrative of the present invention and not limiting.

EXAMPLE 1

In the preferred embodiment of the invention, the therapeutic composition contains plasma-derived C1-esterase inhibitor as the active ingredient, prepared according to Voogelaar E. F. et al., 1974, *Vox Sang.* 26: 118. The virus safety of this preparation is guaranteed by the addition of hepatitis B-immunoglobulin and a heat treatment of the freezed-dried preparation in the final container. Brummelhuis H. G. J. et al., 1983, *Vox Sang.* 45: 205, Tersmette et al., 1986, *Vox Sang.* 51: 239. C1-esterase inhibitor is prepared from human plasma, depleted of vitamin K-dependent coagulation factors, according to a procedure which involves the following purification steps: 1) the starting plasma is 1 to 10 diluted with sterile destined water; 2) the diluted plasma is incubated with DEAE-Sephadex A50 (Pharmacia Fine Chemicals, Uppsaia, Sweden) at a concentration of 2 g/kg, for 60 minutes at 8–10° C.; 3) the DEAE-Sephadex is collected and washed with 150 mM sodium chloride, pH 7.0, and eluted with 10 mM trisodium citrate, 2 M sodium chloride, pH 7.0; 4) ammonium sulphate is added to the eluate to yield a final concentration of 50%, v/v; 5) after centrifugation at 13,000 rpm, ammonium sulphate is added to the supernatant to yield a final concentration of 65%, v/v; 6) the precipitate is collected by centrifugation and dissolved in 10 mM trisodium citrate, pH 7.0; 7) a diafiltration is performed to remove the ammonium sulphate and to concentrate the solution to a protein concentration of 40–50 mg/ml; 8) after the addition of Hepatitis immunoglobulin (0.4 IU/ml), the solution is filtered through a 0.22 μm filter, dispensed in vials and freeze-dried; 9) the freeze-dried product is heat-treated for 72 hours at 60° C.

In the preferred embodiment of the invention, C1-esterase inhibitor will be administered by intravenous injection. For parenteral administration, freeze-dried heat-treated C1-esterase inhibitor is dissolved into water for injections. The final concentration of functional C1-esterase inhibitor in the preparation to be administered may be about 50 U per ml.

EXAMPLE 2

The usage of animal models for AMI is well-known in the art. A model frequently used by investigators is to induce AMI in dogs by occluding the left anterior descending coronary artery (LAD). The usefulness of administering C1-esterase inhibitor as a therapeutic treatment for AMI will be illustrated using this model. Experimental details of the model are given elsewhere. Hermens W. Th et al., 1990, *Circulation* 81 : 649.

Thoracotomy was performed in Mongrel dogs of either sex, after appropriate premedication and anaesthesia. Then, a snare (Mersilene; 3 metric) was placed around the LAD, which had been dissected, distal to the first diagonal branch, and fixed into a polyethylene tube in such a way that an outward pull over a distance of 2 cm caused complete ligation of the LAD. In addition, a catheter (Tygon S 50 HL1) was inserted through the auricle of the left atrium for microsphere injection, collection of blood samples and administration of medication. The thorax was closed and the dogs were allowed to recover. After one week the LAD was occluded after appropriate medication of the dogs, by pulling the snare 2 cm out of the polyethylene tube. Occlusion was verified by electrocardiography and by inspection of the site of occlusion at the end of the experiment. At various time intervals regional myocardial flow was determined by injecting $3-5\times10^6$ tracer microspheres (New England Nucear Corp.; diameter 15 μm) labeled with different isotopes. After 48 hours the animals were killed with an overdose of sodium pentobarbital. The hearts were excised, rinsed and further processed. The right ventricle was removed, the left was cut from base to apex into 5 slices 1–2 cm thick. These slices were then cut into 108 pieces totally. Each piece was weighed. Residual activity of the intracellular enzyme α-hydroxybutyrate dehydrogenase as well as the radioactivity of the tracer micro-spheres were measured in each piece of tissue. The relation between impaired regional myocardial flow after the occlusion and the myocardial cell damage can be visualized by plotting the activity of the tracer microspheres injected 15 minutes after the occlusion versus residual β-hydroxybutyrate for each tissue piece. In non-treated dogs that undergo a permanent occlusion of the LAD, a linear correlation between regional myocardial flow at 15 minutes after the occlusion and myocardial cell damage at 48 hours, exists (FIG. 1A and FIG. 2A). This correlation is altered in dogs that undergo a permanent occlusion of the LAD and who are treated with intravenous injections of C1-esterase inhibitor at a dose of 35 U per kg so body weight at 2 and 8 hours after the occlusion. In these latter animals significantly more residual β-hydroxybutyrate activity is found in the myocardial tissues pieces, in particular in the endocardial tissue pieces, than is expected based on the regional myocar,:dial flow at 15 minutes after the occlusion (FIG. 1B and FIG. 2B), illustrating that administration of C1-esterase inhibitor to the dogs significantly reduces myocardial cell damage after permanent occlusion of the LAD. Similarly, in non-treated animals with permanent occlusion of the LAD, there is a linear correlation between regional myocardial blood flow at 15 minutes and that at 48 hours after occlusion (FIG. 3A and FIG. 4A). C1-esterase inhibitor treatment of dogs with permanent occlusion of the LAD is accompanied by a better flow at 48 hours than is expected based on the flow at 15 minutes after the occlusion (FIG. 3B and FIG. 4B, which suggests that the treatment with C1-esterase inhibitor is able to partially restore regional blood flow in the jeopardized myocardium.

What is claimed is:

1. A therapeutic or prophylactic treatment method of acute myocardial infarction, which method comprises administering exogenous C1-esterase inhibitor, alone or in combination with other drugs, to a patient with acute myocardial infarction or to a patient at risk for acute myocardial infarction.

2. The method of claim 1 where said C1-esterase inhibitor is administered in an amount sufficient to reduce myocardial cell injury.

3. The method of claim 1 where said C1-esterase inhibitor is administered by intravenous injection, usually in an amount in the range of 30 to 40 U per kg of body weight.

4. The method of claim 1 where said C1-esterase inhibitor is C1-esterase inhibitor purified from human plasma.

5. The method of claim 1 where said C1-esterase inhibitor is C1-esterase inhibitor purified from human plasma, and thereafter modified by chemical or other manipulations with maintenance of C1-esterase inhibitor activity.

6. The method of claim 1 where said C1-esterase inhibitor is C1-esterase inhibitor purified from animal plasma.

7. The method of claim 1 where said C1-esterase inhibitor is C1-esterase inhibitor purified from animal plasma, and thereafter modified by chemical or other manipulations with maintenance of C1-esterase inhibitor activity.

8. The method of claim 1 where said C1-esterase inhibitor is C1-esterase inhibitor purified from human biological material other than plasma.

9. The method of claim 1 where said C1-esterase inhibitor is C1-esterase inhibitor purified from human biological material other than plasma, and thereafter modified by chemical or other manipulations with maintenance of C1-esterase inhibitor activity.

10. The method of claim 1 where said C1-esterase inhibitor is C1-esterase inhibitor purified from animal biological material other than plasma.

11. The method of claim 1 where said C1-esterase inhibitor is C1-esterase inhibitor purified from animal biological material other than plasma, and thereafter modified by chemical or other manipulations with maintenance of C1-esterase inhibitor activity.

12. The method of claim 1 where said C1-esterase inhibitor is recombinant C1-esterase inhibitor.

13. The method of claim 1 where said C1-esterase inhibitor is recombinant C1-esterase inhibitor modified by chemical or other manipulations with maintenance of C1-esterase inhibitor activity.

14. The method of claim 1 where said C1-esterase inhibitor is a variant of recombinant C1-esterase inhibitor in which C1-esterase inhibitor activity has been maintained.

15. The method of claim 1 where said C1-esterase inhibitor is a variant of recombinant C1-esterase inhibitor modified by chemical or other manipulations with maintenance of C1-esterase inhibitor activity.

16. The method of claim 1 where said C1-esterase inhibitor is recombinant proteinase inhibitor other than C1-esterase inhibitor, mutated to yield C1-esterase inhibitor activity.

17. The method of claim 1 where said C1-esterase inhibitor is recombinant proteinase inhibitor other than C1-esterase inhibitor, mutated to yield C1-esterase inhibitor activity and modified by chemical or other manipulations with maintenance of C1-esterase inhibitor activity.

18. The method of claim 1 where said C1-esterase inhibitor is administered in combination with a substance which improves the blood flow to the myocardium, such as tissue plasminogen activator, urokinase or streptokinase.

19. The method of claim 1 where said C1-esterase inhibitor is administered in combination with a substance having anti-inflammatory properties, such as an oxygen radical scavenger or a cytokine antagonist.

20. A pharmaceutical composition comprising exogenous C1-esterase inhibitor, a carrier and a substance capable of improving blood flow to the myocardium.

21. A pharmaceutical composition comprising exogenous C1-esterase inhibitor, a carrier and a substance having anti-inflammatory properties.

* * * * *

UNITED STATES PATENT AND TRADEMARK OFFICE

CERTIFICATE OF CORRECTION

PATENT NO. : 6,090,777
DATED : July 18, 2000
INVENTOR(S) : Hack, et al.

It is certified that error appears in the above-identified patent and that said Letters Patent are hereby corrected as shown below:

In Columns 9 and 10, Lines 67 and 1, reads "of Hepatitis immunoglobin" should read --of Hepatitis B immunoglobin--;

In Columns 10, Line 63, reads "myocar,:dial flow" should read --myocardial flow--.

Signed and Sealed this

Seventeenth Day of April, 2001

Attest:

NICHOLAS P. GODICI

Attesting Officer

Acting Director of the United States Patent and Trademark Office